United States Patent [19]

Hosta Pujol et al.

[11] 4,053,483

[45] Oct. 11, 1977

[54] DERIVATIVES OF 3,3-BIS-(4-HYDROXYPHENYL)-2-INDOLINONE AND PROCESS FOR THE PREPARATION THEREOF

[75] Inventors: Alfonso Hosta Pujol; Salvador Brosa Rabassa, both of Barcelona, Spain

[73] Assignee: Doctor Andreu S.A., Spain

[21] Appl. No.: 573,406

[22] Filed: May 1, 1975

[30] Foreign Application Priority Data

May 18, 1974 Spain .................................... 426436

[51] Int. Cl.$^2$ .......................................... C07D 209/34
[52] U.S. Cl. ............................................. 260/325 R
[58] Field of Search .................................. 260/325 R

[56] References Cited

U.S. PATENT DOCUMENTS 3,901,912  8/1975  Brugzese et al. ............... 260/325 R

FOREIGN PATENT DOCUMENTS 1,292,472  10/1972  United Kingdom ............ 260/325 R

OTHER PUBLICATIONS

Garrido et al., Eur. J. Med. Chem., Mar., 1975, No. 2 pp. 142–146.
Moreto et al., Eur. Journ. Pharmacology, 36(1), Mar. 1976, pp. 221–226.
Queralt et al., Archiv de Farm. Y Toxicol., 1(2), Aug. 1975, pp. 137–146.
Wexler et al., "Chem. Abstracts," vol. 69, p. 9977, No. 106, 525g (1968).
Wexler, "Chem. Abstracts," vol. 58, p. 3379g and subject index, p. 1149s (1963).

*Primary Examiner*—Ethel G. Love
*Attorney, Agent, or Firm*—McGlew and Tuttle

[57] ABSTRACT

This invention relates to a group of compounds derived from 3,3-bis-(4-hydroxyphenyl)-2-indolinone having an effective laxative activity. The process for their preparation comprises reacting a substituted 3,3-bis-(4-hydroxyphenyl)-2-indolinone with a compound of the group comprising ethyl chloroformiate, chloracetyl chloride, acetyl chloride, acetyl anhydride, propionyl chloride, propionyl anhydride and chlorosulphonic acid (in pyridine).

4 Claims, No Drawings

DERIVATIVES OF 3,3-BIS-(4-HYDROXYPHENYL)-2-INDOLINONE AND PROCESS FOR THE PREPARATION THEREOF

FIELD OF THE INVENTION

The present invention relates to a new group of compounds derived from 3,3-bis-(4-hydroxyphenyl)-2-indolinone responding to the following structural formula:

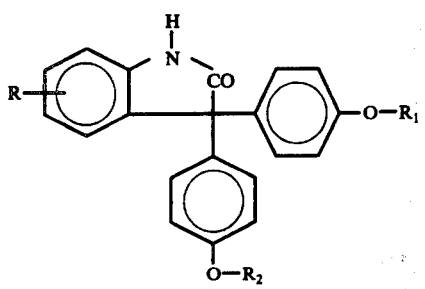

(I)

wherein:
R may be hydrogen, methyl, lower alkyls, methoxy, halogen, nitro, amino, substituted amino and amido in any of the positions of the benzene ring.

$R_1$ and $R_2$ may be the same or different and may be represented by hydrogen, -COOEt, acetyl, chloracetyl, propionyl, -SO$_3$H or the alkali, alkali earth or organic salts thereof.

These derivatives of 3,3-bis-(4-hydroxyphenyl)-2-indolinone have been subjected to various pharmacological tests and their effective laxative activity has been proved.

The invention relates also to the process for preparing said compounds.

This process uses, as starting material, the corresponding aniline (II) which is reacted with chloral hydrate and hydroxylamine hydrochloride to give a substituted isonitroso-acetotoluidide (III) which, when cycled with sulphuric acid and heat gives the corresponding substituted isatin (IV) as per the following diagram:

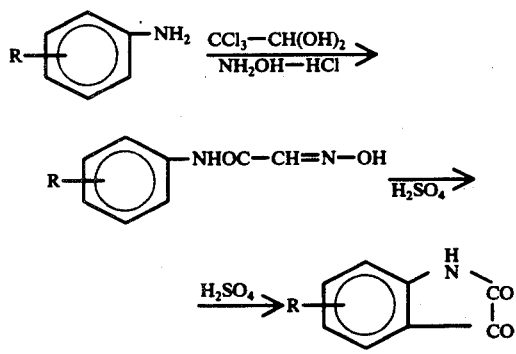

The substituted isatin (IV) is reacted with phenol in the presence of a catalytic amount of concentrated sulphuric acid, using PhOAc, AcOEt, AcOBut or glycol diacetate, alone or in combination, as solvents to give 3,3-bis-(4-hydroxyphenyl)-2-indolinone (V) according to the following diagram:

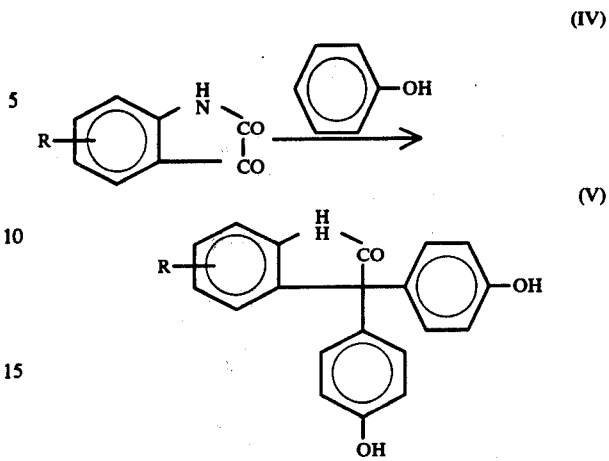

The essence of the process is to react the corresponding 3,3-bis-(4-hydroxyphenyl)-2-indolinone (V) with a compound of the group comprising ethyl chloroformiate, chloracetyl chloride, acetyl chloride or or anydride, propionyl chloride or anhydride and chlorosulphonic acid (in pyridine) to give the compounds (I) of the invention.

DETAILED DESCRIPTION

To facilitate the understanding of the above ideas, hereinafter certain examples of the process of the present invention are described. In view of the purely illustrative nature thereof, such examples should be considered as devoid of any limiting effect with respect to the scope of protection sought.

EXAMPLE I

Preparation of 7-methylisatin 45 g (0.27 mole) of chloral hydrate and 600 ml water were placed in a 3 liter reaction vessel. To this solution there were added in the following order: 650 g of crystallised sodium sulphate (i.e. 286.5 g of anhydrous sodium sulphate + 363.5 ml water), a solution of 27 g (0.25 mole) of o-toluidine in 150 ml water to which 25.6 g (21.5 ml) concentrated hydrochloric acid has been added to dissolve the amine and, finally, a solution of 55 g (0.79 mole) of hydroxylamine hydrochloride in 250 ml water. The mixture was heated in such a way with mechanical stirring that vigorous boiling started after 40-45 minutes. It was allowed to boil for two minutes and then to cool. It was filtered at reduced pressure and the solid was dried in a dissecator at reduced pressure to give 38-40 g (86%) of isonitroso aceto-o-toluidide, m.p. 145°-150° C (discomp.).

Thereafter 300 g of concentrated sulphuric acid was heated at 50° C in a 500 ml flask with mechanical stirring, 40 g of isonitroso aceto-o-toluidide was added at such a rate that the temperature was held between 60°-70° C. Thereafter the temperature was riased to 80° C and held for 10 minutes, after which the mixture was cooled and poured over 12 times its volume of crushed ice. It was allowed to cool (1-2 hours) and filtered, followed by washing with water and drying at reduced pressure to obtain 27 g of 7-methylisatin, m.p. 259°-266° C. Recrystallised in water, m.p. 266° C. Yield 66.5%.

By operating in the same was as in Example I 5-methylisatin, 5-methoxyisatin and 7-methoxyisatin were prepared.

EXAMPLE II

Preparation of 3,3-bis-(4-hydroxyphenyl)-7-methyl-2-indolinone 38.2 g of pure phenol were mixed with 0.4 g of concentrated sulphuric acid, with stirring and heating to 60° C. 28.5 g (0.177 mole) of 7-methylisatin were added in portions. At the end of the addition, the temperature was raised to 85° C and 21 g of PhOAc were gradually added dropwise over a period of 5 hours. Finally, the temperature of the stirred mixture was raised to 120° C for 30 minutes. It was then allowed to cool, filtered and washed with abundant water to remove the PhOAc. The resulting solid was dried and gave 50 g. It was dissolved in acetone and precipitated with chloroform, allowed to cool and filtered. The solid formed was dried to yield 30 g of 3,3-bis-(4-hydroxyphenyl)-7-methyl-2-indolinone, m.p. 272°–4° C. Yield: 52%.

By operating in the same way as in Example II, chromatographically pure 3,3-bis-(4-hydroxyphenyl)-2-indolinone, m.p. 272°–3° C (acetone-chloroform), 3,3-bis-(4-hydroxyphenyl)-5-methyl-2-indolinone, m.p. 271°–3° C (acetone-chloroform) and 3,3-bis-(4-hydroxyphenyl)-5-methoxy-2-indolinone, m.p. 272-3° C (acetone-chloroform) were prepared.

EXAMPLE III

Preparation of the disodium salt of 3,3-bis-(4-sulphoxyphenyl)-7-methyl-2-indolinone 20.4 g of chlorosulphonic acid were added dropwise to a solution of 23.86 g of 3,3-bis-(4-hydroxyphenyl)-7-methyl-2-indolinone in 150 ml of anyhydrous pyridine and the temperature was held to between 0°–5° C. The mixture was stirred for 2 hours at room temperature and then for 7 hours at 45°–50° C. The solution was poured over 600 ml of water/ice, alkalised with 30% sodium hydroxide and extracted with ether to remove the pyridine. Then it was decolourised with activated carbon, filtered and raised to pH 8 with dilute 15% hydrochloric acid. The aqueous solution was washed with chloroform and evaporated to dryness under reduced pressure. The solid residue was washed with ether, filtered and dissolved in 600 ml of boiling methanol. The filtrate was filtered while hot and concentrated to give 32 g of a white solid. This was dissolved in methanol and precipitated with ether, thereafter filtered and digested with hot ethanol. Finally it was filtered and dried. The remaining solid weighed 12 g and was identified as the disodium salt of 3,3-bis-(4-sulphoxyphenyl)-7-methyl-2-indolinone, with m.p. above 360° C.

By operating in the same way as Example III, the following products were prepared:
- the disodium salt of 3,3-bis-(4-sulphoxyphenyl)-5-methyl-2-indolinone, by reaction of 3,3-bis-(4-hydroxyphenyl)-5-methyl-2-indolinone with chlorosulphonic acid, followed by alkalisation with sodium hydroxide or sodium bicarbonate. This was a solid product with m.p. above 360° C.
- the disodium salt of 3,3-bis-(4-sulphoxyphenyl)-5-methoxy-2-indolinone, by a reaction of 3,3-bis-(4-hydroxyphenyl)-5-methoxy-2-indolinone with chlorosulphonic acid, followed by alkalisation with sodium hydroxide or sodium bicarbonate. This was a solid product with m.p. above 360° C.

EXAMPLE IV

Preparation of 3,3-bis-(4-oxicarboethoxyphenyl)-7-methyl-2-indolinone 13.26 g (0.04 mole) of 3,3-bis-(4-hydroxyphenyl)-7-methyl-2-indolinone where dissolved in a solution of 4,2 g of sodium hydroxide in 400 ml water. The solution was then cooled externally with brine until the temperature thereof fell to below 0° C. The solution was stirred while 11.28 g of ethyl chloroformiate were added dropwise, the temperature being held at 0° C. The mixture was stirred for 1 hour at room temperature and filtered. The solid was washed with abundant water and then dried at reduced pressure. Recrystallised in absolute ethanol, it gave 4–5 g of a white product with m.p. 177°–179° C identified as 3,3-bis-(4-oxycarboethoxyphenyl)-7-methyl-2-indolinone.

By operating in the same way as Example IV, the following products were prepared:
3,3-bis-(4-oxycarboethoxyphenyl)-5-methyl-2-indolinone by reaction of 3,3-bis-(4-hydroxyphenyl)-5-methyl-2-indolinone with ethyl chloroformiate. This was a solid product with m.p. 183°–5° C when recrystallised in 45% ethanol.
3,3-bis-(4-oxycarboethoxyphenyl)-5-methoxy-2-indolinone by reaction of 3,3-bis-(4-hydroxyphenyl)-5-methoxy-2-indolinone with ethyl chloroformiate. This was a solid product with m.p. 171°–3° C when recrystallised in 45% ethanol.

EXAMPLE V

Preparation of the sodium salt of 3-(4-hydroxyphenyl)-3-(4-sulphoxyphenyl)-2-indolinone 6.35 g (0.02 mole) of 3,3-bis-(4-hydroxyphenyl)-2-indolinone were dissolved in 36 ml of anhydrous pyridine and cooled to 0° C. 2.33 g (0.02 mole) of chlorosulphonic acid were added dropwise over 1 hour, with stirring and with the temperature held to below 0° C. The solution was then stirred overnight at room temperature and then alkalised with a 5–10% aqueous sodium bicarbonate solution. After washing with chloroform, the aqueous phase was decanted off and the mixture was adjusted to pH 7.5 with dilute hydrochloric acid. The solution was then filtered and decolourised with activated carbon. It was filtered again and evaporated to dryness. The residue was extracted with 60 ml of boiling ethanol. The ethanol solution was filtered and decolourised with activated carbon, filtered again and the filtrate concentrated to give a solid residue which, recrystallised in ethanol, yielded 3 g of a pure solid, identified as the sodium salt of 3-(4-hydroxyphenyl)-3-(4-sulphoxyphenyl)- 2-indolinone.

By operating in the same way as Example V, the following products were prepared:
- the sodium salt of 3-(4-hydroxyphenyl)-3-(4-sulphoxyphenyl)-5-methyl-2-indolinone.
- the sodium salt of 3-(4-hydroxyphenyl)-3-(4-sulphoxyphenyl)-7-methyl-2-indolinone.
- the sodium salt of 3-(4-hydroxyphenyl)-3-(4-sulphoxyphenyl)-5-methoxy-2-indolinone.

EXAMPLE VI

Preparation of the sodium salt of 3-(4-acetoxyphenyl)-3-(4-sulphoxyphenyl)-2-indolinone 6.5 g (0.015 mole) of the sodium salt of 3-(4-hydroxyphenyl)-3-(4-sulphoxyphenyl)-2-indolinone and 5.7 g of anhydrous sodium acetate were suspended in 28.5 ml of anhydrous acetic acid. The suspension was stirred for 18 hours at room temperature and then for 1 hour at boiling point. Thereafter the reacton mixture was cooled, filtered and the filtrate was washed with an excess of ether. A solid crystallised out. This was filtered and purified by crystallisation in ethanol-ether (twice) to produce the sodium salt of 3-(4-acetoxyphenyl)- 3-(4-sulphoxyphenyl)-2-indolinone, weight 4.3 g, yield 60%. It was a white solid with m.p. 190°–200° C with discomposition, and showed the presence of the ester function carbonyl group towards 1760 cm$^{-1}$ in its IR spectrum.

EXAMPLE VII

Preparation of 3,3-bis-(4-chloracetoxyphenyl)-2-indolinone 3.17 g (0.01 mole) of 3,3-bis-(4-hydroxyphenyl)-2-indolinone were suspended in 50 ml of anhydrous pyridine and cooled to 0° C. 2.82 g (0.025 mole) of chloracetyl chloride were added dropwise with stirring, the temperature of 0° C being held. The reaction mixture was held for 12 hours at room temperature and then acidified with dilute hydrochloric acid. It was extracted with ether, washed with water, the ether phase was decanted off, and the mixture was dried over anhydrous sodium sulphate. It was then filtered and the ether was removed from the filtrate at reduced pressure. The solid residue was recrystallised to give 3,3-bis-(4-chloracetoxyphenyl)-2-indolinone, with m.p. 267°–70° C and showing the presence of the ester function carbonyl group in its IR spectrum towards 1720 cm$^{-1}$.

What we claim is:
1. A compound selected from the group consisting of 3,3-bis-(4-sulphoxyphenyl)-7-methyl-2-indoline, and the alkali metal or alkaline earth metal salts thereof.
2. The disodium salt of 3,3-bis-(4-sulphoxyphenyl)-7-methyl-2-indolinone.
3. 3,3-bis-(4-sulphoxy-phenyl)-7-methyl-2-indolinone.
4. 3,3-bis-(4-oxicarboethoxyphenyl)-7-methyl-2-indolinone.

* * * * *